US012521723B2

(12) United States Patent
Jeong et al.

(10) Patent No.: US 12,521,723 B2
(45) Date of Patent: Jan. 13, 2026

(54) POLYMERASE CHAIN REACTION APPARATUS AND POLYMERASE CHAIN REACTION METHOD USING SAME

(71) Applicant: KOREA ADVANCED INSTITUTE OF SCIENCE AND TECHNOLOGY, Daejeon (KR)

(72) Inventors: Ki-Hun Jeong, Daejeon (KR); Young Seop Lee, Daejeon (KR); Byoung-Hoon Kang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 1247 days.

(21) Appl. No.: 17/058,444

(22) PCT Filed: May 29, 2019

(86) PCT No.: PCT/KR2019/006420

§ 371 (c)(1),
(2) Date: Nov. 24, 2020

(87) PCT Pub. No.: WO2019/231230

PCT Pub. Date: Dec. 5, 2019

(65) Prior Publication Data

US 2021/0205816 A1 Jul. 8, 2021

(30) Foreign Application Priority Data

May 31, 2018 (KR) ........................ 10-2018-0062365
Feb. 20, 2019 (KR) ........................ 10-2019-0019825

(51) Int. Cl.

*B01L 7/00* (2006.01)
*B01L 99/00* (2010.01)
*C12Q 1/686* (2018.01)

(52) U.S. Cl.

CPC ......... *B01L 7/52* (2013.01); *B01L 2200/0663* (2013.01); *B01L 2300/0861* (2013.01);

(Continued)

(58) Field of Classification Search

CPC ..... B01L 2200/0663; B01L 2300/0861; B01L 2300/12; B01L 2300/16; B01L 2300/18;

(Continued)

(56) References Cited

U.S. PATENT DOCUMENTS

2015/0049332 A1 2/2015 Sun et al.

FOREIGN PATENT DOCUMENTS

JP 2018500035 A 1/2018
KR 20060094521 8/2006

(Continued)

OTHER PUBLICATIONS

International Search Report from corresponding International Application No. PCT/KR2019/006420, Sep. 6, 2019, pp. 1-2, Korean Intellectual Property Office, Daejeon, Republic of Korea.

(Continued)

*Primary Examiner* — Lydia Edwards
(74) *Attorney, Agent, or Firm* — Hauptman Ham, LLP

(57) ABSTRACT

A polymerase chain reaction apparatus according to the present invention comprises: a transparent photothermal substrate including a transparent plate having an array of transparent nano-pillars arranged to be spaced apart from each other, and plasmonic metal nano-islands disposed on surfaces including upper surfaces and side surfaces of the nano-pillars; a light source disposed under the photothermal substrate and emitting light to the plasmonic metal nano-islands; and a chamber receiving a fluid heated by the transparent photothermal substrate.

8 Claims, 6 Drawing Sheets

1000

(52) U.S. Cl.
CPC ....... *B01L 2300/12* (2013.01); *B01L 2300/16* (2013.01); *B01L 2300/18* (2013.01); *C12Q 1/686* (2013.01)

(58) Field of Classification Search
CPC ................. B01L 7/52; B01L 2200/147; B01L 2300/0822; B01L 2300/0896; B01L 2300/168; B01L 2300/1872; C12Q 1/686
See application file for complete search history.

(56) References Cited

FOREIGN PATENT DOCUMENTS

| | | | | |
|---|---|---|---|---|
| KR | 100756874 B1 | | 9/2007 | |
| KR | 101253455 | | 4/2013 | |
| KR | 1020130065337 A | | 6/2013 | |
| KR | 1020140122066 A | | 10/2014 | |
| KR | 1020140140886 A | | 12/2014 | |
| KR | 1020170008045 A | | 1/2017 | |
| KR | 20170106995 | | 9/2017 | |
| KR | 1020180000831 U | | 3/2018 | |
| WO | WO-2008115626 A2 | * | 9/2008 | ........ B01L 3/502715 |
| WO | WO-2017019768 A1 | * | 2/2017 | ........ B01L 3/502707 |

OTHER PUBLICATIONS

Notice of Allowance dated Nov. 23, 2020 for corresponding case No. KR 10-2019-0019825. (pp. 1-5).

* cited by examiner

[FIG. 1]
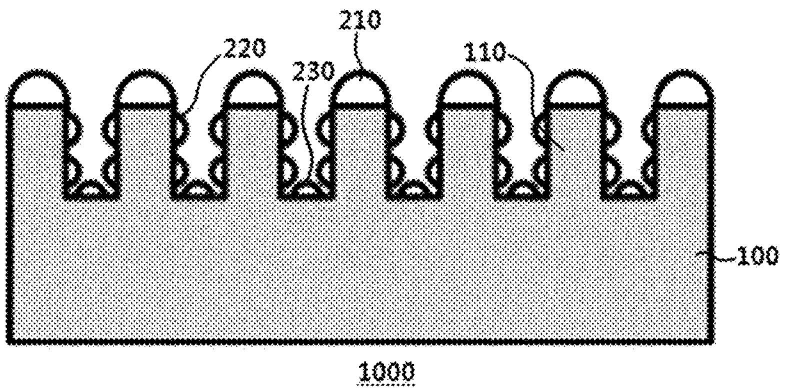
[FIG. 2]
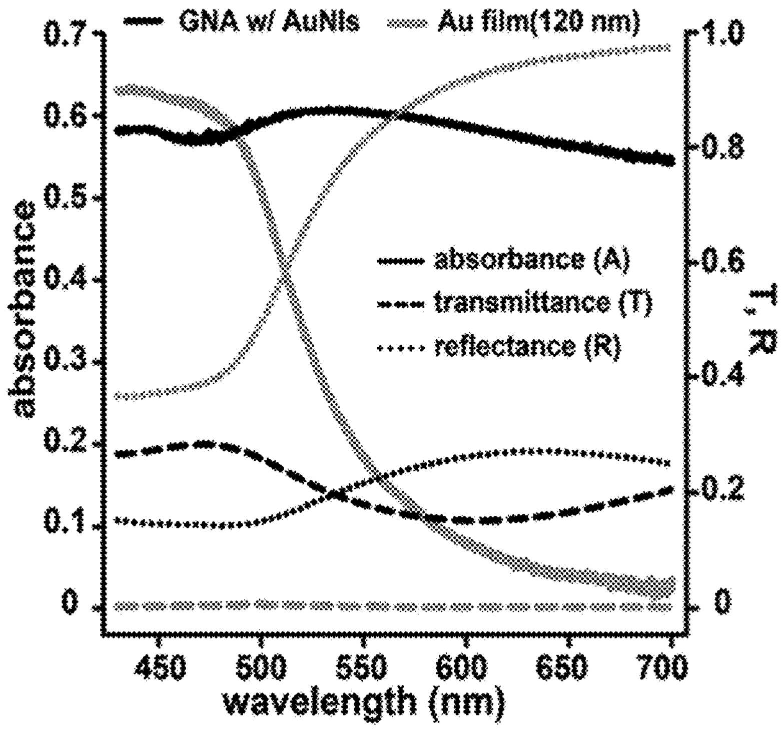

[FIG. 3]
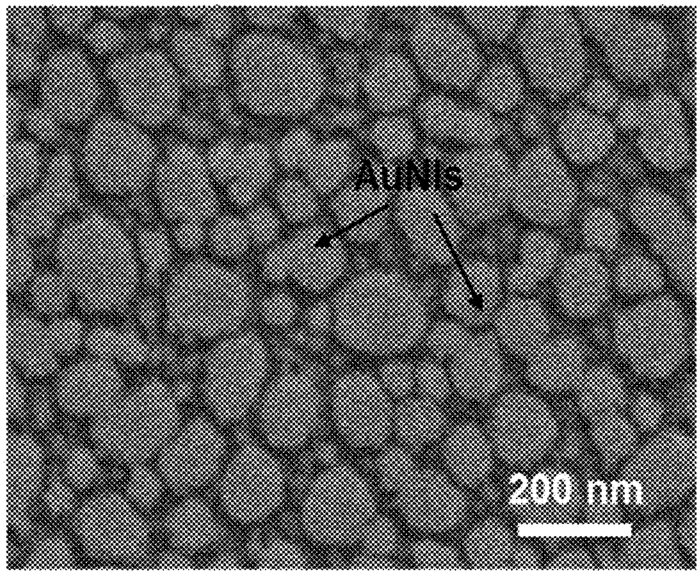
[FIG. 4]
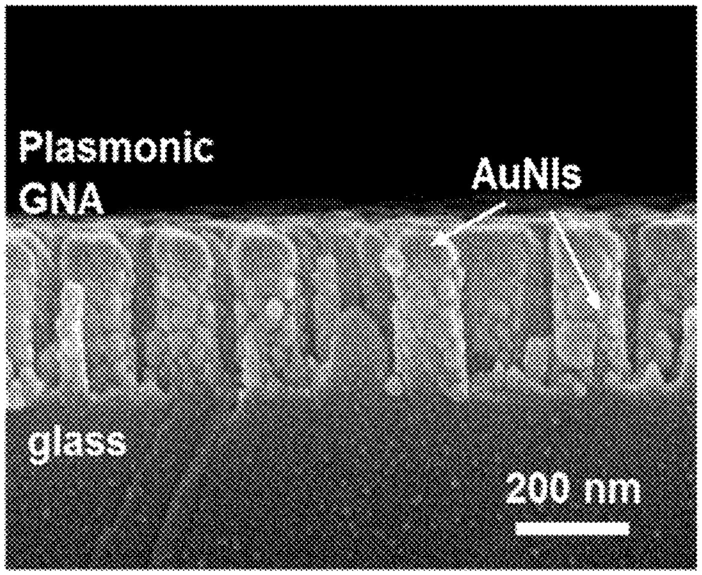

[FIG. 5]
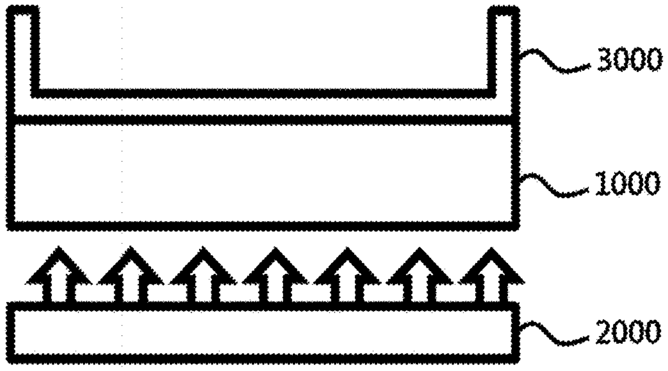
[FIG. 6]
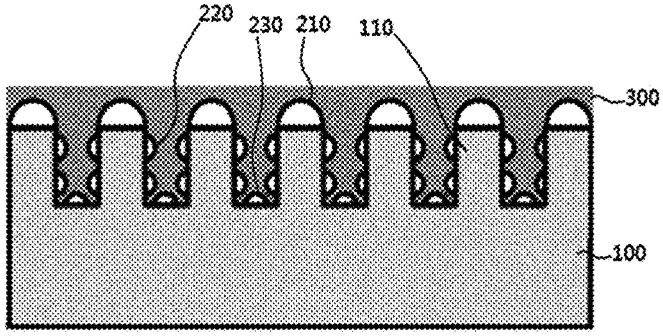
[FIG. 7]
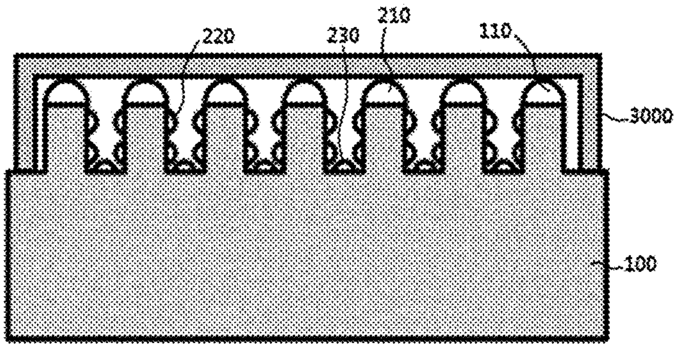

[FIG. 8]
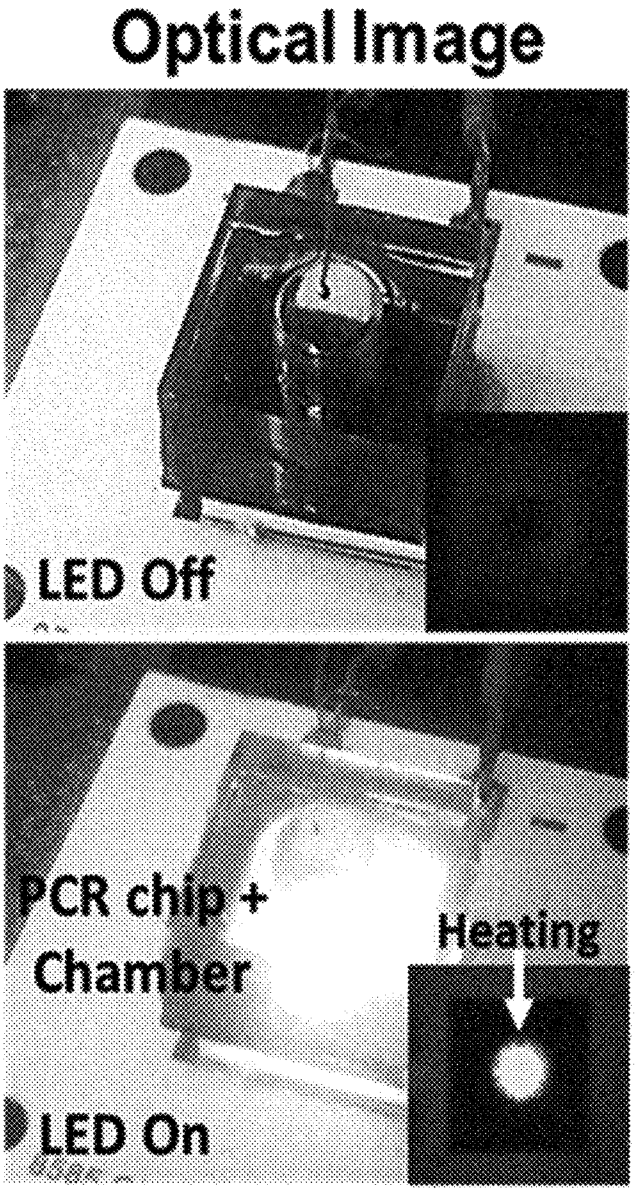

[FIG. 9]
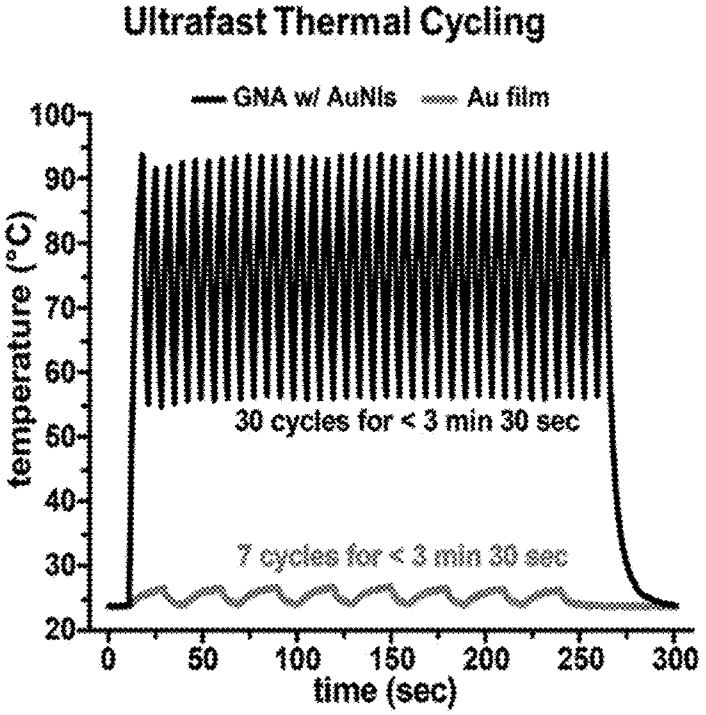
[FIG. 10]
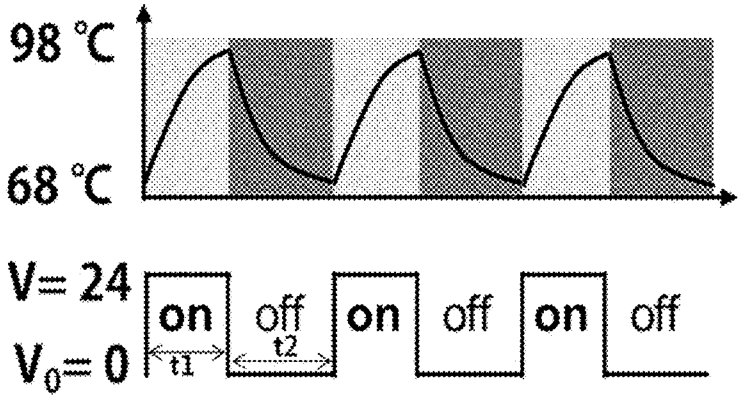

[FIG. 11]
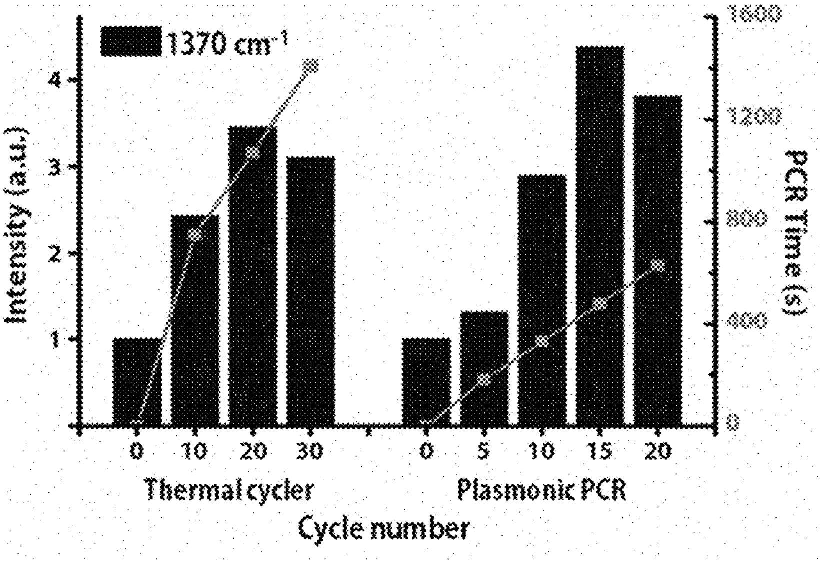
[FIG. 12]
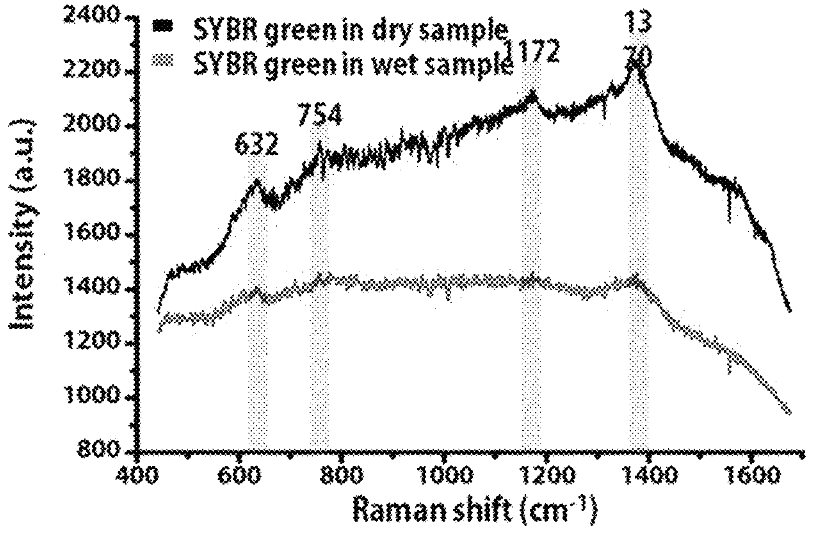

POLYMERASE CHAIN REACTION APPARATUS AND POLYMERASE CHAIN REACTION METHOD USING SAME

RELATED APPLICATIONS

The present application is a U.S. National Phase of International Application Number PCT/KR2019/006420, filed May 29, 2019, and claims priority to Korean Application No. 10-2018-0062365, filed May 31, 2018, and Korean Application No. 10-2019-0019825, filed Feb. 20, 2019.

TECHNICAL FIELD

The present invention relates to a polymerase chain reaction apparatus and a polymerase chain reaction method using the same, and more particularly, to a polymerase chain reaction apparatus which is rapid, simple, and easily used and has high portability to allow point-of-care, and a polymerase chain reaction method using the same.

BACKGROUND ART

Molecular diagnosis plays an important role in various fields ranging from medical fields to forensic fields and the like by analyzing an intrinsic biomarker (DNA, RNA, protein, and the like). Recently, in the molecular diagnosis fields, a study of a molecular diagnosis method for point-of-care (POC) which allows a timely diagnosis and personalized treatment of various diseases including infectious diseases, cancer, and the like, has been actively conducted. In order to use a molecular diagnosis method for point-of-care, a diagnostic technology should have ASSURED criteria such as being affordable, small, simple, user-friendly, rapid & robust, equipment-free, and disposable.

A polymerase chain reaction (PCR) is a technology to amplify nucleic acids and a core technology which is essentially used in a molecular biological diagnostic method. Specifically, PCR is a method using a characteristic of replicating DNA by a DNA polymerase, and the DNA polymerase may synthesize complementary DNA using single stranded DNA as a template and the single stranded DNA may be simply obtained by boiling double stranded DNA. This process is referred to as DNA denaturation. In order for the DNA polymerase to start DNA replication, a start site should be in the form of double stranded DNA. Therefore, in PCR, small DNA pieces, which may be complementarily annealed to template DNA at both ends of a DNA sequence to be amplified, should be added together, and this should be annealed to both ends of a certain DNA sequence to become double stranded DNA. Only in this case, DNA replication by a DNA polymerase may start. A small DNA piece which may be complementarily annealed to the template DNA end is referred to as an oligonucleotide primer or a primer as an abbreviation. After the primer is annealed to the end of the template DNA once, DNA synthesis is extended to the end of the opposite side by the action of the DNA polymerase.

Since a PCR reaction is based on the mechanism described above, a PCR cycle is composed of three steps of a denaturation step of changing double stranded template DNA into single stranded DNA, an annealing step of annealing a primer to the end of template DNA, and an elongation step of extending DNA synthesis to the end of the opposite by the action of a DNA polymerase. After one PCR cycle is finished, in the next PCR cycle, original template DNA and newly synthesized DNA by PCR all become DNA templates. As such, as PCR cycles are continuously repeated, the number of DNA templates is rapidly increased.

Three steps of denaturation-annealing-elongation are controlled by temperature, and thus, a PCR cycle may correspond to a temperature cycle of denaturation temperature-annealing temperature-elongation temperature. An instrument for PCR to form the temperature cycle is generally referred to as a thermal cycler.

A conventional instrument or thermal cycler for PCR adjusts a temperature of a metal plate to form a temperature cycle based on a Peltier element. The conventional thermal cycle for PCR is widely used in most laboratories and hospitals. However, since the thermal cycler is voluminous and has high power consumption, and it takes a long time to obtain a result, it is inappropriate to be utilized in molecular diagnosis for point-of-care in which diagnosis should be performed in real time.

After a first generation PCR method, various PCR technologies have been studied. For example, a method of increasing a sample surface area exposed to heat using capillaries, a method of using a micro-fluid substrate (Korean Patent Registration No. 10-0756874), a method of using water droplets and a laser, and the like have been reported. However, newly developed PCR technologies also have limitations in direct use in the molecular diagnosis for point-of-care, for example, low portability and decreased amplification efficiency, and requires a treatment by a trained technician, or since it is too expensive to be used for a single use, professional maintenance of the apparatus is required.

DISCLOSURE

Technical Problem

An object of the present invention is to provide a polymerase chain reaction apparatus which may be used in molecular diagnosis for point-of-care and a polymerase chain reaction method using the same.

Another object of the present invention is to provide an ultrafast polymerase chain reaction apparatus and a polymerase chain reaction method using the same.

Still another object of the present invention is to provide a polymerase chain reaction apparatus which allows an amplification degree of a material by a polymerase chain reaction (such as nucleic acid) to be observed in real time, and a polymerase chain reaction method using the same.

Technical Solution

In one general aspect, a polymerase chain reaction apparatus includes a transparent photothermal substrate including a transparent plate on which an array of transparent nanopillars arranged to be spaced apart from each other is formed and plasmonic metal nanoislands positioned on surfaces including an upper surface and a side surface of the nanopillars; a light source which is positioned on a lower portion of the photothermal substrate and irradiates the plasmonic metal nanoislands with a light; and a chamber containing a fluid heated by the transparent photothermal substrate.

In the polymerase chain reaction apparatus according to an exemplary embodiment of the present invention, the plasmonic metal nanoislands may be positioned to be spaced apart from each other.

In the polymerase chain reaction apparatus according to an exemplary embodiment of the present invention, an average diameter of the nanopillars may be 50 to 1000 nm, and an aspect ratio obtained by dividing an average length of the nanopillars by the average diameter of the nanopillar may be 0.1 to 10.

In the polymerase chain reaction apparatus according to an exemplary embodiment of the present invention, a coverage which is, based on one surface of the transparent plate on which the array of nanopillars is positioned, a ratio of an area of the one surface covered by the array of nanopillars to an area of the one surface, may be 0.1 to 0.9.

In the polymerase chain reaction apparatus according to an exemplary embodiment of the present invention, the nanoislands positioned on the upper surface of the nanopillars may have a shape corresponding to the upper surface of the nanopillars, and the nanoislands positioned on the side surface of the nanopillars may have an average diameter of 5 to 100 nm.

In the polymerase chain reaction apparatus according to an exemplary embodiment of the present invention, the photothermal substrate may further include a heat dissipation layer which covers nanopillars on which the plasmonic metal nanoislands are positioned.

In the polymerase chain reaction apparatus according to an exemplary embodiment of the present invention, the light from the light source may be in a visible light to a near-infrared ray.

In the polymerase chain reaction apparatus according to an exemplary embodiment of the present invention, the chamber may have inner space comparted by a lower surface and a side surface and may contain the fluid in the inner space.

In the polymerase chain reaction apparatus according to an exemplary embodiment of the present invention, the chamber is positioned to be in contact with the metal nanoislands positioned on the upper surface of the nanopillars but is extended from an upper plate covering the array of nanopillars so as to surround the upper plate and the array of nanopillars, whereby one extended end may include a side portion in contact with the transparent plate.

In the polymerase chain reaction apparatus according to an exemplary embodiment of the present invention, the polymerase chain reaction apparatus may further include a temperature sensor for measuring a temperature of a space containing a fluid in the chamber or the photothermal substrate.

In the polymerase chain reaction apparatus according to an exemplary embodiment of the present invention, the polymerase chain reaction apparatus may further include a light irradiation control unit for controlling the light source and the light irradiation control unit may control one or more factors selected from a light intensity, a light irradiation time, and a light irradiation cycle.

In the polymerase chain reaction apparatus according to an exemplary embodiment of the present invention, the light irradiation control unit may control the light source so as to conform to a preset temperature profile.

In the polymerase chain reaction apparatus according to an exemplary embodiment of the present invention, the polymerase chain reaction apparatus may further include a detector for detecting a Raman signal generated from the fluid.

The present invention includes a polymerase chain reaction method using the polymerase chain reaction apparatus described above.

In another general aspect, the polymerase chain reaction method using the polymerase chain reaction apparatus described above includes: a) adding a fluid which is subject to a polymerase chain reaction to a chamber; and b) irradiating the transparent photothermal substrate with a light generated from a light source so that the fluid conforms to a temperature profile over time.

In the polymerase chain reaction method according to an exemplary embodiment of the present invention, one or more factors selected from a light intensity irradiated on the transparent photothermal substrate, a light irradiation time, and a light irradiation cycle may be controlled to satisfy the temperature profile over time.

In the polymerase chain reaction method according to an exemplary embodiment of the present invention, the temperature profile over time may be a profile in which a temperature rise from an annealing temperature to a denaturation temperature and a temperature reduction from a denaturation temperature to an annealing temperature are set to a cycle and the cycle is repeated.

The polymerase chain reaction method according to an exemplary embodiment of the present invention may further include: in the middle of the step b) or after the step b), irradiating the fluid with an excitation light for Raman scattering or the light from the light source to perform surface enhanced Raman scattering analysis.

Advantageous Effects

The polymerase chain reaction apparatus according to the present invention converts light energy into thermal energy, based on a plasmonic photothermal effect by a transparent photothermal substrate including a transparent plate on which an array of transparent nanopillars arranged to be spaced apart from each other and plasmonic metal nanoislands positioned on surfaces including an upper surface and a side surface of the nanopillars, thereby having a high absorbance and a high-efficiency photothermal effect in a visible light region, and allows ultrafast temperature change and an ultrafast polymerase chain reaction thereby to more rapidly and efficiently amplify nucleic acids (such as DNA, RNA, and cDNA) than a conventional polymerase chain reaction technology. In addition, the polymerase chain reaction apparatus according to the present invention may be manufactured at low costs to have excellent commerciality and also have portability to be used as a molecular diagnostic tool for point-of-care as well as molecular diagnosis at a laboratory level.

In addition, in the polymerase chain reaction apparatus according to the present invention, a transparent photothermal substrate generating a plasmonic photothermal effect includes a transparent plate on which an array of transparent nanopillars are arranged to be spaced apart from each other and plasmonic metal nanoislands positioned on surfaces including an upper surface and a side surface of the nanopillars to have a surface enhanced Raman scattering activity, thereby allowing an amplification degree of nucleic acids to be measured in real time, together with amplification of nucleic acids.

DESCRIPTION OF DRAWINGS

FIG. 1 is a cross-sectional view illustrating a transparent photothermal substrate in the PCR apparatus according to an exemplary embodiment of the present invention.

FIG. 2 is a drawing illustrating absorbance for each light wavelength of the transparent photothermal substrate according to an exemplary embodiment of the present invention.

FIG. 3 is a scanning electronic microscope photograph in which an upper portion of the transparent photothermal substrate manufactured according to an exemplary embodiment of the present invention is observed.

FIG. 4 is a scanning electronic microscope photograph in which a side portion of the transparent photothermal substrate manufactured according to an exemplary embodiment of the present invention is observed.

FIG. 5 is a drawing illustrating an apparatus diagram of the PCR apparatus manufactured according to an exemplary embodiment of the present invention.

FIG. 6 is one cross-sectional view illustrating another example of the transparent photothermal substrate, in an exemplary embodiment of the present invention.

FIG. 7 is a drawing illustrating the transparent photothermal substrate and a chamber, in an exemplary embodiment of the present invention.

FIG. 8 is a drawing illustrating an optical photograph of the PCR apparatus manufactured according to an exemplary embodiment of the present invention and a temperature mapping result of the chamber depending on whether light was irradiated.

FIG. 9 is a drawing illustrating measured temperature cycle characteristics depending on control of light irradiation in the PCR apparatus manufactured according to an exemplary embodiment of the present invention.

FIG. 10 is a drawing illustrating a set temperature profile and control conditions of a light source implementing the temperature profile, in the PCR apparatus manufactured according to an exemplary embodiment of the present invention.

FIG. 11 is a drawing illustrating results of analyzing amplified DNA by SERS, using the PCR apparatus manufactured according to an exemplary embodiment of the present invention.

FIG. 12 is a drawing illustrating results of spectroscopically analyzing DNA in the middle of an amplification process by surface enhanced Raman scattering in real time, using the PCR apparatus manufactured according to an exemplary embodiment of the present invention.

BEST MODE

Hereinafter, the polymerase chain reaction apparatus of the present invention and the polymerase chain reaction method using the same will be described in detail, with reference to the attached drawings. The drawings to be provided below are provided by way of example so that the idea of the present invention can be sufficiently transferred to a person skilled in the art to which the present invention pertains. Therefore, the present invention is not limited to the drawings provided below but may be embodied in many different forms, and the drawings suggested below may be exaggerated in order to clear the spirit of the present invention. Technical terms and scientific terms used herein have the general meaning understood by those skilled in the art to which the present invention pertains unless otherwise defined, and a description for the known function and configuration which may unnecessarily obscure the gist of the present invention will be omitted in the following description and the accompanying drawings.

The PCR apparatus according to the present invention includes a transparent photothermal substrate including a transparent plate on which an array of transparent nanopillars arranged to be spaced apart from each other is formed and plasmonic metal nanoislands positioned on surfaces including an upper surface and a side surface of the nanopillars; a light source which is positioned on a lower portion of the photothermal substrate and irradiates the plasmonic metal nanoislands with a light; and a chamber containing a fluid heated by the transparent photothermal substrate.

The PCR apparatus according to the present invention is a PCR apparatus based on a plasmonic photothermal effect in which nanoislands of a plasmonic metal which is a metal having a plasmonic activity are positioned on surfaces including an upper surface and a side surface of each transparent nanopillar forming an array of transparent nanopillars, thereby strongly absorbing light energy by plasmonic metal nanoislands and emitting the absorbed light energy as thermal energy.

FIG. 1 is a cross-sectional view illustrating a transparent photothermal substrate 1000 in the PCR apparatus according to an exemplary embodiment of the present invention, in which the transparent photothermal substrate 1000 includes a transparent plate 100 on which an array of transparent nanopillars 110 arranged to be spaced apart from each other is formed and plasmonic metal nanoislands 210 and 220 positioned on surfaces including an upper surface and a side surface of the nanopillars, as in an example illustrated in FIG. 1.

In addition, on the transparent photothermal substrate 1000, metal nanoislands 230 may be positioned also on a surface of the transparent plate between the nanopillars, together with the metal nanoislands 210 positioned on the upper surface of each nanopillar 110 and the metal nanoislands 220 positioned on the side surface of each nanopillar 110, as in an example illustrated in FIG. 1.

That is, on the transparent photothermal substrate 1000, the plasmonic metal nanoislands 210, 220, and 230 may be positioned on an area including the upper surface and the side surface of each nanopillar 110 forming the array of transparent nanopillars and the surface of the transparent plate exposed between the nanopillars 110.

Here, the nanoisland of the metal islands 210, 220, and 230 may mean a state in which the plasmonic metal positioned on the transparent photothermal substrate 1000 is not connected to each other to form a continuum. Here, a standard of the continuum may be determined by whether the plasmonic metal is continuously connected from the upper surface (surface of one end) of a pillar to a lower end (the other end) of the pillar, in a pillar length direction of the nanopillars. In other words, the plasmonic metal nanoislands may be in a state of being positioned to be spaced apart from each other, and be randomly positioned but be in a state of being spaced apart from each other.

Absorption of light energy by the plasmonic metal nanoislands may include absorption of light energy by surface plasmon resonance (SPR) of the metal nanoislands 210, 220, and 230 positioned on the transparent photothermal substrate 1000, localized surface plasmon resonance (LSPR) generated in hot-spots between the metal nanoislands 220 or between the metal nanoislands 210 and the metal nanoislands 220 positioned on one nanopillar 110, and localized surface plasmon resonance (LSPR) generated in hot-spots between the metal nanoislands 210 and 220 positioned on one nanopillar and the metal nanoislands 210 and 220 positioned on another nanopillar in nanopillars adjacent to each other.

The hot-spots between the metal nanoislands may include hot-spots between the metal nanoislands 210 positioned on the upper surface of the nanopillars adjacent to each other, and therewith or independently thereof, the hot-spots between the metal nanoislands may include hot-spots between the metal nanoislands positioned on the side surface of the nanopillars adjacent to each other (between the metal nanoislands 210 belonging to nanopillars 110 adjacent to each other).

Furthermore, the hot-spots between the metal nanoislands may include hot-spots between the metal nanoislands 230 positioned on the surface of the transparent plate, and therewith or independently thereof, between the metal nanoisland 220 positioned on the side surface of one nanopillar 110 and the metal nanoisland 230 positioned on the surface of the transparent plate.

FIG. 2 is a drawing illustrating absorbance for each light wavelength of the transparent photothermal substrate (GNA w/AuNIs of FIG. 2) according to an exemplary embodiment of the present invention and absorbance for each light wavelength of an Au thin film (thickness of 120 nm, an Au film of FIG. 2). Here, the absorbance is calculated from a transmittance (T) and a reflectance (R) illustrated in FIG. 2 together with the absorbance.

Specifically, the transparent photothermal substrate of FIG. 2 is a photothermal substrate obtained by washing a 4 inch borosilicate glass substrate with a sulfuric acid and a hydrogen peroxide solution, depositing a silver (Au) film having a thickness of 10 nm using thermal deposition, performing annealing at 300° C. for 30 minutes to convert the silver thin film into silver nanoislands by solid-state dewetting, using the silver nanoislands as an etching mask and removing a silver mask remaining after dry etching (reactive ion etching) of the glass substrate by wet etching with a silver etchant to produce a glass substrate on which an array of glass nanopillars is formed, and thereafter, depositing gold (Au) on the glass substrate on which the array of glass nanopillars is formed using thermal deposition to form Au nanoislands on the upper surface and the side surface of the glass nanopillars and the surface of the glass substrate exposed between the glass nanopillars. Here, a dry etching time was adjusted to adjust a length of nanopillars and a gold deposition time was adjusted to control a size and a density of metal nanoislands. Specifically, dry etching was performed for 86 seconds under conditions of $CF_4$ of 15 sccm, $CHF_3$ of 45 sccm, Ar of 150 sccm, a pressure of 0.2 torr, and an RF power of 300 W, and thermal deposition of gold (Au) was performed until Au nanoislands having a thickness of 30 nm were formed on the upper surface of the glass nanopillars. A method of forming a metal mask which is an etching mask, a method of forming an array of nanopillars, and a method of forming metal nanoislands may be performed with reference to the published patents of the present applicant (KR 2014-0140886, KR 2017-0008045, and KR 2018-0000831), and the present invention includes the descriptions of the published patents of the present application regarding the method of forming a metal mask which is an etching mask, the method of forming an array of nanopillars, and the method of forming metal nanoislands (KR 2014-0140886, KR 2017-0008045, and KR 2018-0000831) by reference.

As seen from FIG. 2, the transparent photothermal substrate according to an exemplary embodiment of the present invention has various hot-spots in which strong local electric fields such as LSPR between the metal nanoislands positioned on one nanopillar, LSPR between the metal nanoislands belonging to each of the nanopillars adjacent to each other, and LSPR between the metal nanoislands positioned on the side surface of the nanopillars and the metal nanoislands positioned on the transparent substrate, together with SPR of the plasmonic metal nanoislands themselves are enhanced, thereby having a high light absorbance in a broad optical band. In addition, since the nanopillars themselves are irregularly (randomly) spaced apart from each other and the metal nanoislands formed on the nanopillars are also irregularly (randomly) positioned on the side surface to be spaced apart from each other, even the same kind of LSPR (as an example, LSPR between the metal nanoislands positioned on one nanopillar) has different LSPR wavelengths from each other, and thus, the transparent photothermal substrate may have an excellent light absorbance of 0.5 or more to light in a visible light to near-infrared ray region, in particular, in an entire visible light region.

However, it was found that the Au thin film represents a light absorbance of 0.5 or more in a region of 400-500 mm where absorption by the plasmonic characteristic of Au occurs, but as the light wavelength is increased to more than 500 nm, a light absorbance is rapidly decreased and the light absorbance at a wavelength of 600 nm was less than 0.1.

Since the transparent photothermal substrate according to an exemplary embodiment of the present invention has an excellent light absorbance of 0.5 or more to light in the visible light to near-infrared ray region, in particular, the entire visible light region (400-700 nm), a photothermal effect may be generated by simple visible light irradiation which does not cause optical damage to a biochemical material including nucleic acids, and light energy is absorbed with an extremely excellent light absorbance in the entire wavelength region of 400 to 700 nm, and thus, higher thermal energy may be generated in such case than in the case in which the same size of light energy is irradiated.

In the PCR apparatus according to an exemplary embodiment of the present invention, being "transparent" may mean having a transmittance of light, specifically a visible light (400-700 nm) to a near-infrared ray (0.78-3 μm), specifically visible light of 90% or more, more specifically 95% or more, and still more specifically 98% or more.

The transparent plate may be any material as long as it is an insulating material transparent to light, specifically a light in a visible light to a near-infrared ray, and more specifically a visible light. As a substantial example, the transparent plate may be transparent inorganic materials such as glass, transparent polymers such as polymethylmethacrylate (PMMA), polydimethylsiloxane (PDMS), and polyurethane acrylate (PUA), and the like, but is not limited thereto.

The transparent nanopillar may be the same or different materials as/from the transparent plate, and may be any material as long as it is an insulating material transparent to light, specifically a light in a visible light to a near-infrared ray, and more specifically a visible light. As a substantial example, the nanopillars may be transparent inorganic materials such as glass, transparent polymers such as polymethylmethacrylate (PMMA), polydimethylsiloxane (PDMS), and polyurethane acrylate (PUA), and the like, but are not limited thereto.

An average diameter of the nanopillars forming the array of nanopillars may be 50 to 1000 nm, specifically 100 to 500 nm, and more specifically 100 to 300 nm, and an aspect ratio obtained by dividing an average length of the nanopillars by the average diameter may be 0.1 to 10, specifically 1 to 10, more specifically 1.5 to 7, and still more specifically 1.5 to 4. The average diameter and the aspect ratio of the nanopillars are the size and the aspect ratio at which even the same kind of LSPR may form various LSPR wavelengths by arrangement of metal nanoislands having a large size distribution and irregular (random) metal nanoislands to show a high light absorbance of 0.55 or more in the entire wavelength region of 400-700 nm, and simultaneously, are the size and the aspect ratio at which excellent mechanical (physical) stability may be secured, a large amount of heat may be generated by a photothermal effect, and the generated heat may be rapidly conducted to a fluid, but the present invention is not necessarily limited thereto.

A coverage which is a ratio of an area of one surface covered with the array of nanopillars to an area of one surface, based on the one surface of the transparent plate on which the array of nanopillars, may be 0.10 to 0.90, specifically 0.40 to 0.85, and more specifically 0.50 to 0.85.

A ratio of an area (coverage) of one surface of the transparent plate covered with the array of nanopillars affects heat generated per a unit area of the transparent photothermal substrate, and the coverage described above is a coverage at which uniform heating or temperature change of a fluid may occur even in the transparent photothermal substrate having a large area up to 4 inches, but the present invention is not necessarily limited thereto.

The metal of the metal nanoislands may be any metal having a plasmon activity. As a specific example, the metal of the metal nanoislands may be noble metals such as gold, platinum, and silver, copper, nickel, aluminum, and the like, and may be gold in terms of biocompatibility, but the present invention is not necessarily limited thereto.

In the transparent photothermal substrate, the nanoislands (210 of FIG. 1) positioned on the upper surface of the nanopillars may have a shape corresponding to the upper surface (shape of the upper surface) of the nanopillars. Specifically, the nanoislands positioned on the upper surface of the nanopillars may have a shape and a size corresponding to the shape and the size (diameter) of the upper surface of the nanopillars, and may cover the upper surface of the nanopillars. Substantially, the nanoislands 210 may have a disc shape or a truncated particle shape. According to a specific example, when the nanoislands positioned on the upper surface of the nanopillars have a disc shape, the side surface may have a convex curvature. According to a specific example, when the nanoislands positioned on the upper surface of the nanopillars have a truncated particle shape, the surface except a truncated surface may have a smoothly curved shape and may have a shape pressed in parallel, but is not necessarily limited thereto. The nanoislands 210 positioned on the upper surface of the nanopillars may have a thickness of 10 to 50 nm, specifically 10 to 40 nm, but is not limited thereto.

In addition, the nanoislands 220 positioned on the side surface of the nanopillars or the nanoislands 230 positioned on the surface of the transparent plate between the nanopillars may have a circular shape, an ellipsoidal shape, or an irregular shape, and the metal nanoislands 220 and 230 may have an average diameter of 5 to 100 nm. As a specific example, the metal nanoislands 220 and 230 may have an average diameter of 5 to 100 nm, specifically 5 to 50 nm, and more specifically 5 to 30 nm, and an average of 4 to 10 metal nanoislands may be positioned to be spaced apart in a length direction of nanopillars.

FIG. 3 is a scanning electron microscope photograph in which the upper portion of the actually manufactured transparent photothermal substrate described above based on FIG. 2 is observed, and FIG. 4 is a scanning electron microscope photograph in which the side portion of the actually manufactured transparent photothermal substrate described above based on FIG. 2 is observed.

As seen from FIGS. 3 and 4, it is seen that the transparent nanopillars are irregularly arranged to form the array of nanopillars on the manufactured transparent photothermal substrate, and the transparent nanopillars have an average diameter of 100 nm, an average height of 180 nm, and a surface fill factor of about 0.55. It is seen that the metal nanoislands positioned on the upper surface of the nanopillars have a size (diameter) and a shape corresponding to the upper surface of each nanopillar on which the nanoislands are positioned, and have a disc shape having a thickness of 30 nm. In addition, it is seen that the metal nanoislands positioned on the surface except the upper surface of the nanopillars have a size of 50 nm and a space of 10 nm or less, and are positioned to be spaced apart from each other, but are randomly positioned.

The plasmonic metal nanoislands 210, 220, and 230 may have a truncated particle shape, specifically a truncated spherical shape, and the truncated part may form an interface with the nanopillars 110 or the transparent plate 100.

FIG. 5 is a drawing illustrating an apparatus diagram of the PCR apparatus according to an exemplary embodiment of the present invention. As in an example of FIG. 5, the light source 2000 is positioned on the lower portion of the transparent photothermal substrate 1000 and the array of nanopillars on which the metal nanoislands of the transparent photothermal substrate 1000 are present may be irradiated with light.

The light from the light source may be in a visible light to a near-infrared ray. The visible light may be a light belonging to a region of 400 to 700 nm and the near-infrared ray may be a light belonging to a region of 0.78 to 3 μm. For a high light absorbance, prevention of damage to a biochemical material including nucleic acids, and generation of a more rapid and uniform photothermal effect, the irradiated light from the light source is advantageously a visible light. Here, the visible light does not mean only a white light, and may include a red light, a green light, a blue light, or a combination thereof, of course. That is, the light source may include a combination including a red light source, a green light source, a blue light source, or a white light source.

However, as described above, the transparent photothermal substrate 1000 according to a specific example of the present invention may have an extremely high light absorbance of 0.5, substantially 0.55 or more in the entire visible light region (400-700 nm). Thus, a light having a single wavelength may be irradiated, but the light source is advantageously a white light source so that more heat may be generated in a shorter time. Substantially, the white light source may be a halogen lamp, a xenon lamp, a white LED, or the like, but is not necessarily limited thereto. Here, if necessary, a white light (visible light) from which ultraviolet rays and the like generated from the light source are removed may be irradiated using a filter or the like, of course.

In addition, as in an example illustrated in FIG. 5, the chamber 3000 may be positioned on the upper portion of the transparent photothermal substrate 1000, and may have an inner space comparted by the lower surface and the side surface and may contain a fluid in the inner space. The inner space of the chamber is a housing space to house the fluid for PCR and an area where the reaction occurs.

In an example of FIG. 5, an example in which a single chamber 3000 is provided on one transparent photothermal substrate 1000, but two or more chambers 3000 may be provided to be spaced apart from each other on the one transparent photothermal substrate 1000, of course, and the chambers may contain the same fluid or different fluids from each other, of course. Since the chamber is comparted to have a space containing the fluid containing an analyte (such as a biochemical material), it may be referred to as a well. A shape of the chamber 3000 may be a circular shape or a polygonal shape of a rectangular to octagonal shape, and may have a diameter of several mm to several cm, or on the other hand, or may be a microchamber (microwell) having a diameter of 1000 μm or less.

The fluid (fluid for PCR) may be a solution including a target nucleic acid, a nucleic acid polymerase, and a primer pair to amplify the target nucleic acid (including a buffer solution), but is not necessarily limited thereto, and may be any common composition used in PCR. The target nucleic acid means all nucleic acids to be amplified by an amplification reaction of PCR and the like, and as an example, may be nucleic acids such as DNA, RNA, and cDNA containing a single or a plurality of nucleotide polymorphisms.

FIG. 6 is a cross-sectional view illustrating another example of the transparent photothermal substrate 1000, and as in an example illustrated in FIG. 6, the transparent photothermal substrate 1000 may further include a heat dissipation layer 3000 covering nanopillars 110 on which the plasmonic metal nanoislands 210 and 220 are positioned.

The heat dissipation layer 300 may serve to more rapidly transfer heat generated by the plasmonic photothermal effect to the chamber, and also, may serve to neutralize surface charges.

The heat dissipation layer 300 may be any material having a similar or higher value of thermal conductivity as compared with the thermal conductivity of the transparent plate. As a specific example, the heat dissipation layer 300 may be inorganic materials such as a-Si, $SiO_2$, and hydrogen silsesquioxane (HSQ), polymers such as polydimethylsiloxane (PDMS), and the like, and may have a thickness of 1 nm to 100 μm, but is not limited thereto. In addition, in FIG. 6, an example in which the array of nanopillars is all embedded in the heat dissipation layer 300 is illustrated, but the present invention is not limited thereto, and the heat dissipation layer may be provided in the form of a thin film of several to several tens of nanometers to maintain unevenness by the nanopillars itself, of course.

FIG. 7 is a cross-sectional view illustrating the transparent photothermal substrate 1000 and the chamber 3000, in an exemplary embodiment of the present invention. As in an example illustrated in FIG. 7, the chamber 3000 is positioned to be in contact with the metal nanoislands 210 positioned on the upper surface of the nanopillars 110 but is extended from the upper plate so as to surround the upper plate covering the array of nanopillars and the array of nanopillars, so that one extended end may include a side portion in contact with the transparent plate.

An empty space between the nanopillars 110 on which the metal nanoislands are formed may correspond to the inner space containing the fluid in the chamber 3000, and also, the chamber 3000 may be further provided with an inlet for injecting the fluid and a through hole for venting in an edge area.

Since the empty space between the nanopillars 110 becomes the space containing the fluid, the metal nanoislands generating the plasmonic photothermal effect may be brought into direct contact with the fluid. Thus, heat generated by light may directly heat the fluid and the temperature of the fluid may be controlled more rapidly and uniformly, and also, the temperature may be controlled so that the fluid injected by light control very accurately conforms to the temperature profile set as a whole.

The material of the chamber 3000 illustrated in an example of FIG. 5 or FIG. 7 is not reacted with a nucleic acid, and is not particularly limited as long as it is a transparent insulating material. As a specific example, the chamber may be transparent inorganic materials such as glass, transparent polymers such as polymethylmethacrylate (PMMA), polydimethylsiloxane (PDMS), polyurethane (PU), polypropylene (PP), and polyurethane acrylate (PUA), and the like, but is necessarily not limited thereto.

The polymerase chain reaction apparatus according to an exemplary embodiment of the present invention may further include a temperature sensor for measuring the temperature of the space containing the fluid in the photothermal substrate or the chamber. The temperature sensor may be any apparatus to measure the temperature of the housing space in the chamber, such as a thermographic camera and a thermocouple. The temperature sensor may be unnecessary when PCR is in progress, but may be required when the values of control factors of the light source are set so as to conform to the set temperature profile.

The polymerase chain reaction apparatus according to an exemplary embodiment of the present invention may further include a light irradiation control unit for controlling the light source, and the light irradiation control unit may control one or more factors selected from a light intensity, a light irradiation time, and a light irradiation cycle.

Specifically, the light irradiation control unit may control the light source so as to conform to the preset temperature profile, and may control one or more factors selected from a light intensity, a light irradiation time, and a light irradiation cycle, so as to conform to the preset temperature profile. Here, the light irradiation control unit may control at least one or more factors selected from a light intensity, a light irradiation time, and a light irradiation cycle, so as to conform to the preset temperature profile based on information of the temperature sensor input by output of the temperature sensor.

The control of the light irradiation time may include control of irradiation forms such as pulse irradiation or continuous irradiation. Control of a light irradiation cycle may include on/off control of light, and pulse irradiation may include control of a pulse width and an interval between pulses. The light intensity may include a light intensity over time (constant or changed intensity), and the pulse irradiation may include control of a maximum value (intensity) and a minimum value (intensity) (including 0) forming the pulse. The light intensity may be controlled by voltage, current, and the like applied to the light source, of course.

The temperature profile over time is a preset temperature profile, and may be in a state in which controlled values of one or more factors selected from a light intensity, a light irradiation time, and a light irradiation cycle has been previously input to the light irradiation control unit so as to conform to the corresponding temperature profile by the previous experiment. On the other hand, one or more factors selected from a light intensity, a light irradiation time, and a light irradiation cycle may be controlled so as to conform to the temperature profile preset by inputting the output of the temperature sensor.

An example of the temperature profile over time which has been previously input to the control unit may be a profile in which a temperature rise from an annealing temperature to a denaturation temperature and a temperature reduction from a denaturation temperature to an annealing temperature are set to a cycle and the cycle is repeated and a temperature profile in which a temperature rise rate value, a temperature reduction rate value, an annealing temperature value, a denaturation temperature value, a holding time at the annealing temperature (including 0), a holding time at the denaturation temperature, the number of repeated cycles, and the like are predetermined, but the present invention may not be limited to the specific conditions of the temperature profile, of course.

The polymerase chain reaction apparatus according to an exemplary embodiment of the present invention may further include a detector for detecting a Raman signal generated from the fluid. That is, by further including the detector for detecting a Raman signal, material information of nucleic acids amplified by a surface enhanced Raman scattering (SERS) spectroscopy and an amplification degree may be analyzed in real time. Here, when the light source includes the wavelength of an excitation light for Raman scattering, separate laser (laser generating a light of an excitation wavelength) is not needed, but when selectively required, laser generating a light of an excitation wavelength may be further included together with the detector.

The SERS analysis in real time which may be performed together with nucleic acid amplification is based on the facts that the transparent photothermal substrate described above is a substrate provided with hot-spots which may enhance a Raman signal, the wavelength of LSPR present in the transparent photothermal substrate is present in a large wavelength region from 400 to 700 nm, and in particular, as in the chamber of FIG. 7, the fluid may be brought into direct contact with the hot-spots to allow very strong signal enhancement.

Here, when SERS analysis is intended to be performed at the same time, the fluid may further include a Raman prove bound to a target nucleic acid, together with the target nucleic acid, a nucleic acid polymerase, and a primer pair to amplify the target nucleic acid, of course.

The SERS analysis may be performed in real time in the middle of nucleic acid amplification, or otherwise, may be performed after nucleic acid amplification has been completed.

FIG. 8 is a drawing illustrating an optical photograph of a PCR apparatus manufactured by forming a PDMS chamber on the upper portion of the photothermal substrate described above based on FIG. 2 with a similar structure to that of FIG. 5 and disposing a white LED light source (3 W) on the lower portion of the photothermal substrate, and a temperature mapping result, in which it may be confirmed that when the light source was turned off, the temperature inside the chamber was the same as an ambient temperature, and when the light source was turned on, the inside of the chamber was uniformly heated.

FIG. 9 is a drawing illustrating measured temperature cycle characteristics depending on control of light irradiation in the PCR apparatus illustrated in FIG. 8, and in FIG. 9, "GNA w/AuNIs" shown in black is the result of the PCR apparatus illustrated in FIG. 8, and "Au film" shown in gray is the result of an apparatus in which a glass substrate having an Au thin film (thickness of 120 nm) formed thereon in FIG. 2 was used as the transparent photothermal substrate, instead of the transparent photothermal substrate on which the array of nanopillars having metal nanoislands positioned thereon are formed, in the PCR apparatus illustrated in FIG. 8. FIG. 10 is a drawing illustrating a preset temperature profile (repeat of a cycle of annealing temperature (55° C.)->denaturation temperature (93° C.)->annealing temperature (55° C.)) in FIG. 9 and control conditions of the light source implementing the corresponding temperature profile, in which a pulse type white light was irradiated by a white LED light source, the voltage of the light source at the time of pulse application was 24 V, a pulse width (t1) was 4 sec, and an interval between pulses (t2) was 3 sec.

As seen from FIG. 9, it was found that the PCR apparatus according to an exemplary embodiment of the present invention implemented 30 thermal cycles within 3 minutes and 30 seconds, a maximum temperature and a minimum temperature were uniformly controlled without a deviation for each thermal cycle, and the designed temperature (an annealing temperature at 93° C. and a denaturation temperature at 55° C.) was implemented vary accurately.

As seen from the results of an Au film of FIG. 9, it was shown that an ultrafast temperature adjustment (heating & cooling) which may not be implemented in a conventional plasmonic photothermal effect may be implemented by the PCR apparatus according to an exemplary embodiment of the present invention, and ultrafast and ultrahigh-efficiency PCR was implemented. In addition, as described based on an example of FIG. 2, it is seen that a photothermal substrate may be manufactured by a simple process of depositing, annealing, dry etching, wet etching, and depositing, thereby mass-producing the PCR apparatus according to an exemplary embodiment of the present invention at low costs, and as in FIG. 8, since the apparatus has a small, light, and simple apparatus structure of a photothermal substrate, a light source, and a chamber to have portability and mobility and control values are input to the control unit so as to conform to the preset temperature profile to repeatedly implement the temperature cycle, nucleic acids may be amplified stably, effectively, and accurately even by a non-skilled person, and thus, the apparatus is very appropriate for point-of-care (POC).

FIG. 11 is a drawing illustrating a result of nucleic acid amplification using the apparatus illustrated in FIG. 8 (Plasmonic PCR of FIG. 11), and also illustrates a results of amplification by a commercial thermal cycler using a Peltier metal block (thermal cycler of FIG. 11) for comparison.

Specifically, the result of FIG. 11 was obtained by using template λ-DNA (CATCGTCTGCCTGTCATGGGCTGT-TAATCATTACCGTGATAACGCCATTACCTACAAA GCCCAGCGCGACAAAAATGCCAGAGAACT-GAAGCTGGCGA), a Z-Taq DNA polymerase (Takara Bio Inc.), a Z-Taq buffer (Takara Bio Inc.), a nucleoside triphosphate (dNTP, Takara Bio Inc.), a forward primer (Bioneer Inc., 5-CATCGTCTGCCTGTCATGGGCTGTTAAT-3), and a reverse primer (Bioneer Inc., 5-TCGCCAGCTTCAGTTCTCTGGCATTT-3); a fluid for PCR (PCR composition) was prepared by mixing 0.2 μL of the Z-Taq DNA polymerase, 2 μL of the Z-Taq buffer, 1.6 μL of the nucleoside triphosphate, 1.8 μL of the forward primer, 1.8 μL of the reverse primer, 1 μL of the template λ-DNA (1 ng/μL), and 12.4 μL of distilled water; 20 μL of the PCR composition and 30 μL of a mineral oil were successively added to the chamber of the PCR apparatus according to FIG. 8; and the temperature cycle was repeated similar to the above description based on FIGS. 9 and 10 to perform photothermal PCR.

An amplified DNA intensity in FIG. 11 was produced from electrophoresis, a cycle number was the number of repetitions of the temperature cycle performed for amplification, and PCR time(s) means a time (sec) taken when the corresponding number of temperature cycles was repeated.

As seen from FIG. 11, it was found that it took about 1100 seconds to repeat 20 times in the Peltier element-based thermal cycler in which very fast amplification is performed among the conventional PCR technology and it took only about 600 seconds to repeat 20 times in the apparatus according to an exemplary embodiment of the present invention, and in terms of the DNA intensity at the same numbers of the temperature cycle repetitions of 10 and 20, nucleic acid amplification was performed more effectively in the apparatus according to an exemplary embodiment of the present invention than in the conventional thermal cycler when the temperature cycle was repeated at the same number of times.

FIG. 12 is a drawing illustrating a result of irradiating a laser at 633 nm to a fluid in the chamber for a time (t2) when the light source was turned off as in FIG. 10, and detecting a SERS signal emitted from DNA by a spectrometer, in the process of adding a fluid for PCR further including SYBR green with a Raman prove (as described above in FIG. 11) to the apparatus illustrated in FIG. 8 and amplifying nucleic acids by repeating the thermal cycle.

As seen from FIG. 12, it was found that nucleic acid detection by PCR and SERS may be performed at the same time, and information and amplification degree of amplified DNA may be detected "in real time" by SERS measurement.

In the results of FIG. 12, a laser at 633 nm was irradiated with excitation light while the LED white light source was turned off, but when the light source produced a white light including an excitation light wavelength, SERS measurement may be performed only by irradiating light generated from the light source without separate laser irradiation, of course.

The present invention includes a PCR method using the PCR apparatus described above.

The PCR method according to the present invention is a polymerase chain reaction method using the polymerase chain reaction apparatus described above, and includes: a) adding a fluid which is subject to a polymerase chain reaction (fluid for PCR) to a chamber; and b) irradiating the transparent photothermal substrate with a light generated from a light source so that the fluid conforms to a temperature profile over time.

As described above based on the PCR apparatus, the temperature of the fluid may be controlled so as to conform to the preset temperature profile over time by controlling one or more factors selected from a light intensity irradiated on the transparent photothermal substrate, a light irradiation time, and a light irradiation cycle.

Here, the temperature profile over time may be a profile in which a temperature rise from an annealing temperature to a denaturation temperature and a temperature reduction from a denaturation temperature to an annealing temperature are set to a cycle and the cycle is repeated. As a specific example, the annealing temperature may be 50 to 60° C. and the denaturation temperature may be 90 to 98° C., but the temperature profile may be configured with a known annealing temperature and a known denaturation temperature depending on the target nucleic acid which is a nucleic acid to be amplified, a nucleic acid polymerase, and the specific material of the primer pair to amplify the target nucleic acid, of course.

In the middle of the step b) or after the step b), a step of irradiating fluid with an excitation light for Raman scattering or the light from the light source to perform surface enhanced Raman scattering analysis, may be further included. That is, in the PCR method according to an exemplary embodiment of the present invention, nucleic acid detection in real time (nucleic acid detection in real time during an amplification process) using SERS may be simultaneously performed, together with ultrafast and ultrahigh-efficiency nucleic acid amplification.

Hereinabove, although the present invention has been described by specific matters, limited exemplary embodiments, and drawings, they have been provided only for assisting the entire understanding of the present invention, and the present invention is not limited to the exemplary embodiments, and various modifications and changes may be made by those skilled in the art to which the present invention pertains from the description.

Therefore, the spirit of the present invention should not be limited to the above-described exemplary embodiments, and the following claims as well as all modified equally or equivalently to the claims are intended to fall within the scope and spirit of the invention.

The invention claimed is:

1. A polymerase chain reaction apparatus comprising:

a transparent photothermal substrate including a transparent plate on which an array of transparent nanopillars arranged to be spaced apart from each other is formed and plasmonic metal nanoislands positioned on surfaces including an upper surface and a side surface of the nanopillars;

a light source which is positioned on a lower portion of the photothermal substrate and irradiates the plasmonic metal nanoislands with light; and a chamber containing a fluid heated by the transparent photothermal substrate, wherein the plasmonic metal nanoislands are positioned to be spaced apart from each other, the metal is gold, the transparent photothermal substrate is a glass substrate, an average diameter of the nanopillars is 50 to 1000 nm, and an aspect ratio obtained by dividing an average length of the nanopillars by the average diameter of the nanopillar is 0.1 to 10, a coverage, which is defined as a ratio of an area covered by the array of nanopillars to an area of the one side of the transparent plate, is 0.1 to 0.9, the plasmonic metal nanoislands positioned on the upper surface of the nanopillars have a shape corresponding to the upper surface of the nanopillars, and the plasmonic metal nanoislands positioned on the side surface of the nanopillars have an average diameter of 5 to 100 nm, and the photothermal substrate further includes a heat dissipation layer covering the nanopillars on which the plasmonic metal nanoislands are positioned.

2. The polymerase chain reaction apparatus of claim 1, wherein the light from the light source is in a visible light to a near-infrared ray.

3. The polymerase chain reaction apparatus of claim 1, wherein the chamber has an inner space comparted by a lower surface and a side surface, and the inner space contains the fluid.

4. The polymerase chain reaction apparatus of claim 1, wherein the chamber is positioned in contact with the metal nanoislands, which is positioned on the upper surface of the nanopillars, and includes an upper plate covering the metal nanoislands, which is positioned on the array of nanopillars, and a side portion extending from the upper plate to enclose the array of nanopillars, with the extended end of the side portion in contact with the transparent plate.

5. The polymerase chain reaction apparatus of claim 1, further comprising: a temperature sensor for measuring a temperature of a space containing a fluid in the chamber or the photothermal substrate.

6. The polymerase chain reaction apparatus of claim 5, further comprising: a light irradiation control unit for controlling the light source, wherein the light irradiation control unit controls one or more factors selected from a light intensity, a light irradiation time, and a light irradiation cycle.

7. The polymerase chain reaction apparatus of claim 6, wherein the light irradiation control unit controls the light source so as to conform to a preset temperature profile.

8. The polymerase chain reaction apparatus of claim 6, further comprising: a detector for detecting a Raman signal generated in the fluid.

* * * * *